(12) United States Patent
Steinke

(10) Patent No.: US 6,946,102 B2
(45) Date of Patent: Sep. 20, 2005

(54) APPARATUS FOR THE REMEDIATION OF PARTICULATE MATERIAL AND TOXIC POLLUTANTS IN TRANSIT IN FLUE GAS

(76) Inventor: Richard A. Steinke, 1580 Bermuda Dunes Dr., Boulder City, NV (US) 89005

( * ) Notice: Subject to any disclaimer, the term of this patent is extended or adjusted under 35 U.S.C. 154(b) by 737 days.

(21) Appl. No.: 09/893,124

(22) Filed: Jun. 26, 2001

(65) Prior Publication Data

US 2002/0007731 A1 Jan. 24, 2002

Related U.S. Application Data

(63) Continuation-in-part of application No. 09/323,215, filed on Jun. 1, 1999, now abandoned.

(51) Int. Cl.$^7$ .............................................. B01D 50/00
(52) U.S. Cl. ....................... 422/177; 422/168; 422/169; 422/170; 422/171; 422/172; 422/211
(58) Field of Search ................................ 422/168–172, 422/177, 211; 423/242.1, 210, 243.01, 244.01, 244.02, 244.07, 243.08, 243.1

(56) References Cited

U.S. PATENT DOCUMENTS

| | | | | |
|---|---|---|---|---|
| 4,277,450 A | * | 7/1981 | Dilworth | 423/244.08 |
| 4,604,269 A | * | 8/1986 | Yoon | 423/244.07 |
| 4,795,619 A | * | 1/1989 | Lerner | 423/244.08 |
| 4,922,840 A | * | 5/1990 | Woodroffe et al. | 110/345 |
| 5,084,256 A | * | 1/1992 | McElroy et al. | 423/243.08 |

* cited by examiner

Primary Examiner—Basia Ridley
(74) Attorney, Agent, or Firm—M. Reid Russell

(57) ABSTRACT

The invention is in an apparatus for the remediation of particulate material and gaseous pollutants from a flue gas flow that is simple and highly efficient in removing nearly all toxic pollutants, particularly sulfur dioxide, from a flue gas flow, and includes a manifold that is to receive and pass a polluted flue gas flow that mounts an injector that is fitted into the manifold wall to inject finely ground sorbent materials counter-current to the flue gas flow, creating turbulence and a thorough mixing to effect compaction and/or agglomerization of the pollutant and sorbent particles. The invention provides for a sensing of the moisture content of the flue gas flow of the compacted and agglomorized sorbent and pollutant particles and, as needed, as water as a fine or atomized mist a required humidity in the combined particulates as is suitable for particle separation in a particulate removal system as the invention is connected to, with, when the invention is arranged with a bag house particulate removal system, the moisture content of the compacted flue gas and sorbent material particles is maintained at from eighteen to twenty percent humidity.

12 Claims, 3 Drawing Sheets

APPARATUS FOR THE REMEDIATION OF PARTICULATE MATERIAL AND TOXIC POLLUTANTS IN TRANSIT IN FLUE GAS

The present application is a continuation in part application based upon an original application Ser. No. 09/323,215, filed Jun. 1, 1999 now abandoned, entitled: IMPROVED APPARATUS AND METHOD FOR THE REMEDIATION OF PARTICULATE MATERIAL AND TOXIC POLLUTANTS TRANSPORTED IN FLUE GAS.

BACKGROUND OF THE INVENTION

1. Field of the Invention

This invention relates to methods and apparatus for the remediation of particulate matter and toxic flue gas pollutants in transit in a flue gas stream, and in particular to methods and apparatus for removal of materials and pollutants, such as sulfur dioxide, from flue gases produced in coal fired power plants, and the like, by forcing and promoting a reaction between the pollutants and selected sorbent materials.

2. Prior Art

In the combustion of fossil fuels, as for power generation, a variety of particulate matter and gaseous pollutants, some of which are toxic, are produced and discharged as flue gas. Among which are oxides of sulphur, including sulphur dioxide, $SO_2$ oxides of nitrogen and volatile organic compounds. The oxides of sulphur, particularly sulphur dioxide $SO_2$ are generally considered as the most serious and are toxic pollutants. To remove flue gas pollutants, a number of pollution control systems have been developed that remove fine particulate matter and submicron size particles. Some such systems rely on electrostatically charged sorbent particles to attract and agglomerize with unlike charged particles in the flue gas stream, providing particles of a sufficient size to be removed in a moving fluidized bed, by passage through a bag house, in a centrifuge system, or the like. Examples of several such systems that one of the present inventions is a co-inventor of are found in U.S. Pat. No. 5,308,590; 5,312,598; and 5,332,562.

Functionally and structurally distinct from such electrostatic charging system, a system for promoting a reaction between pollutants and sorbent material by providing compaction and mixing of the agglomerized particles of pollutant and sorbent materials for separation in a conventional bag house, centrifuge, or the like, is set out in U.S. patents to one of the present inventors, U.S. Pat. Nos. 5,723,099 and 5,795,549. The above '099 and '549 patents teach a mechanical mixing of sorbent materials into a flue gas stream utilizing a fan or impeller, and a passing of the mixed flow through a venturi. The present invention improves upon these patents by providing a unique injection system for passing a counter-current flow of sorbent materials, under pressure, into the flue gas stream that results in a greatly improved mixing efficiency, and which mixing continues over a long residency period for thorough mixing and agglomerizing together of the sorbent and pollutant particles. Further, the invention measures and controls mix moisture content after flue gas and sorbent mixing to, as needed, add moisture, as a fine pressurized water spray into the flow, so as to obtain an ideal moisture content of the agglomerized particles that makes possible the removal of essential all the pollutant particles from the gas stream as in a bag house, or particulate removal system.

In addition to the above cited U.S. patents to one of the present inventors, a number of systems have been developed and employed that provide for a remediation of toxic flue gases utilizing sorbent material compaction, none of which, however, anticipate the invention. For example, a U.S. Pat. No. 4,061,476 to Holter, et al, provides for delivery of a sorbent material into a gas stream and employs a venture that reduces the passage cross section to stimulate mixing of a sorbent that is then reacted with pollutants in a gas stream. The invention is, of course, distinct from the mixing system of the '476 patent as it relies upon a pressurized flow of sorbent materials injected into a flue gas stream counter-current to the direction of the flue gas flow to provide turbulence and mixing. Like the '099 and '549 patents of one of the present inventors, the Holter, et al '476 patent, and U.S. Patents to Bortz, et al., U.S. Pat. No. 5,165,902; to Teller, U.S. Pat. No. 4,271,134 and to Kimura, U.S. Pat. No. 4,645,653, that is shown also in a European Patent Application, No. 0,226,863, all involve moisturizing of the sorbent materials prior to passage into the flue gas stream. None, however, provide for measuring the moisture content of the mix of sorbent materials and flue gas constituents, like the invention. Nor do they provide for adding water thereto, as needed, to obtain an optimum moisture content of the mix prior to separation of the agglomerized sorbent and pollutant particles as in a bag house, or like particulate removal system.

SUMMARY OF THE INVENTION

It is a principal object of the present invention to provide a simple and efficient remediation apparatus and method for the removal of flue gas pollutants that is inexpensive to produce and maintain.

Another object of the present invention is to provide a remediation apparatus and method that exhibits a greater efficiency in the removal of flue gas pollutants over earlier technology.

Another object of the present invention is to provide a remediation apparatus that includes an arrangement for thoroughly mixing of sorbent materials into a flue gas stream by directing an opposing flow of the sorbent materials, under pressure, a counter-current flow into that flue gas stream and providing for an extended residency of the particulates and sorbent materials whereby the particles and sorbent materials join or agglomorize and are thoroughly mixed and compacted.

Another object of the present invention is to provide a remediation apparatus and method that provides for measuring the humidity level or water content of the compacted sorbent materials and flue gas pollutants and, as needed, adds water in the form of a fine mist to the mix to maintain an optimum moisture content in the thoroughly mixed and compacted flow of particles and sorbent materials that will promote an efficient agglomerized particle separation in a bag house, centrifuge, or the like.

Another object of the present invention is to provide a remediation apparatus that can readily be retrofitted into an existing power plant pollution removal system.

Still another object of the present invention is to provide a remediation apparatus that is simple in its construction and has all the component elements thereof as require periodic maintenance and repair located outside of a flue gas flow manifold or conduit of the invention, with feed sorbent materials and water vapor directed into that conduit or manifold through external lines or pipes.

Still another object of the present invention is to provide a remediation apparatus and method that produce, as a product of the operations thereof, a flow of agglomerized particles made up of compacted sorbent and pollutant materials having a water content that is optimum to facilitate their removal from the gas stream in a bag house, centrifuge, or the like.

Still another object of the present invention is to provide a remediation apparatus and method to produce agglomerized particles containing compacted sorbent materials and pollution particulates from a flue gas stream that have an optimum water content for facilitating removal of the agglomerized particles in a conventional bag house, allowing for a removal of nearly all noxious pollutants from the flue gas stream.

The invention is in a new and improved apparatus and method for the remediation of toxic pollutants in flue gases, and in particular to a very efficient removal of sulphur dioxide ($SO_2$) from the flue gas as is produced by a coal burning power plant. To provide for which pollutants removal of a large percentage to nearly all of the noxious pollutants, in particular sulphur dioxide ($SO_2$), as are present in the flue gas flow, a practice of the invention provides an enhanced mixing and compaction of flue pollutant particles with sorbent material particles and an extended residency together of which particles and materials for effecting an optimal mixing and agglomerization thereof. Whereafter, the water content of which compacted particles is measured and enhanced, as necessary, to an optimum water content percentage for promoting removal of the mixed and agglomerized particulates when the flow is passed into a separation apparatus such as a bag house, centrifuge, or the like.

A preferred embodiment of the invention includes a manifold or tubular housing that is essentially a straight tube that is connected into a flue gas exhaust, presenting an open flow passage therethrough to the flue gases as are produced by a coal fired power generation plant, or the like. An inlet nozzle connects into the manifold at approximately a thirty (30) to sixty (60) degree angle to the flue gas direction of flow, to pass a preferred sorbent material, such as a finely ground lime selected from a family including hydrated lime, quick lime, limestone, or the like, and for some applications, may be a non-lime material such as a phosphorus mixture, carbon compound, compound containing ammonia, or the like, within the scope of this disclosure. The sorbent material is passed, under pressure, through the inlet nozzle and is injected counter-current into the flue gas flow. This sorbent material counter-current injection and reaction chamber length provides turbulence and an extended residency period for the conflicting flows that produces a thorough mixing and results essentially a total compaction of the sorbent particles with pollutant particles in the flue gas stream, agglomerating the particles together. Which agglomerized particles then continue through the manifold, to the manifold exhaust end.

After mixing and compaction in the reaction chamber, the flow is directed across a sensor that measures humidity or water content in the mix and, as needed, adds water, in the form of a fine mist, that is injected through a nozzle into the flow to maintain a moisture or humidity level in the flow that is preferably from eighteen (18) to twenty (20) percent of saturation. In practice, finely ground sorbent particles in a range of from fifty (50) to one hundred fifty (150) mesh are preferred where the remediation system of the invention produces agglomerized particulates for removal in a centrifuge type device. Whereas, where the removal system is a conventional bag house, finer particles are preferred of from one hundred fifty (150) to three hundred fifty (350) mesh. While, when the invention provides compacted materials for removal in a centrifuge system, the moisture content passed from the remediation system of the invention is not as critical. Where particulate removal is to take place in a conventional bag house, the moisture content of the flow as is passed into the bag house is critical. Accordingly, when a bag house system, as herein illustrated, is so utilized, the moisture content of a flow of sorbent and pollutant particles is maintained at between eighteen (18) and twenty (20) percent and, at this moisture content, it has been found in practice, a ninety (90) to ninety-seven (97) and greater percent of pollutant particles, will be removed from the flue gas flow.

BRIEF DESCRIPTION OF THE DRAWINGS

These and other objects of the present invention will become more fully apparent from the following description in which the invention is describe in detail in conjunction with the accompanying drawings.

DETAILED DESCRIPTION OF THE INVENTION

Figure 1:
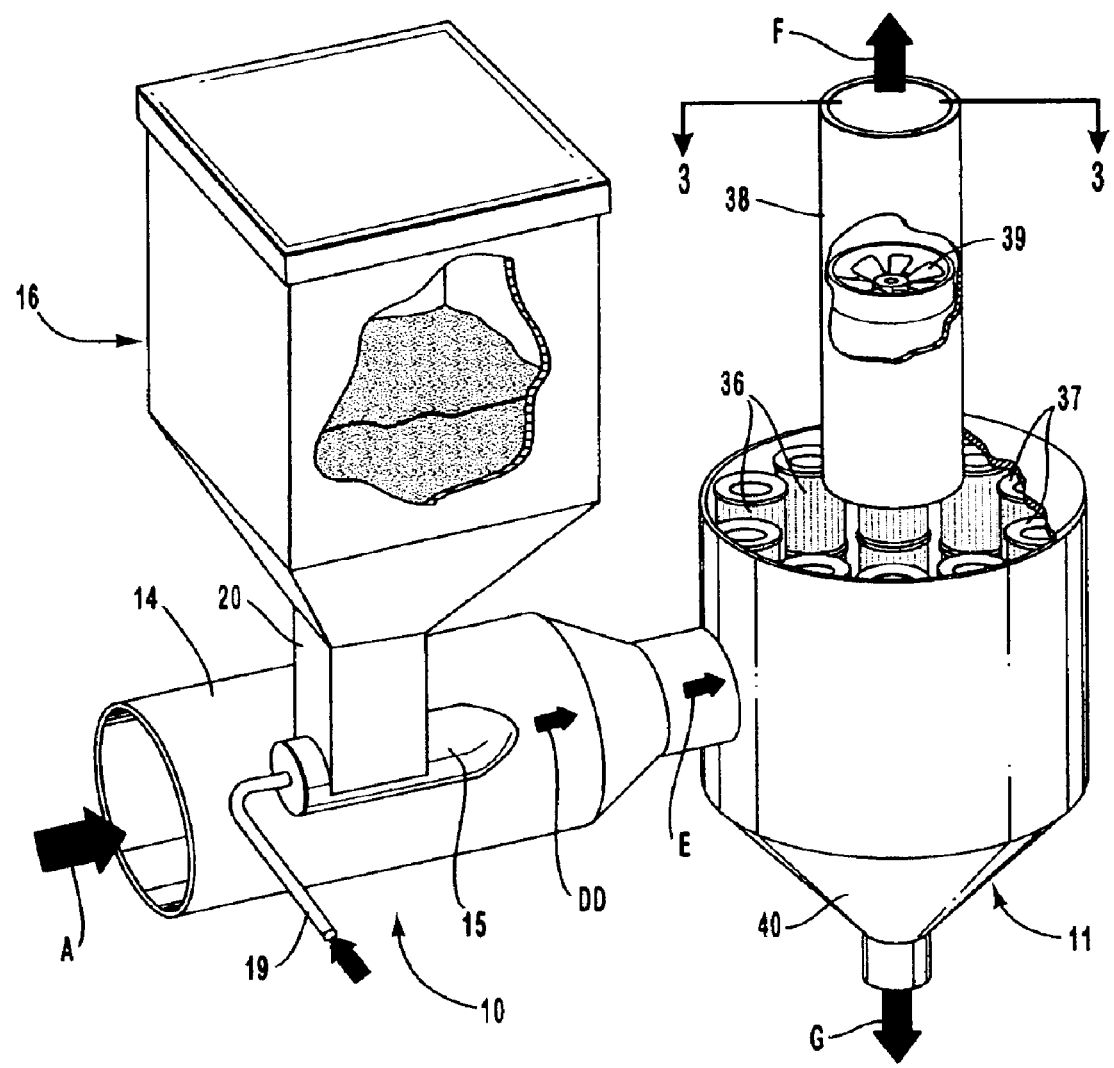
FIG. 1 is a side elevation view of the improved apparatus of the invention for the remediation of toxic flue gas pollutants shown passing a flow of compacted and moisturized particles of sorbent material and flue gas pollutants into a bag house, that removes the compacted particulates from the flow.

Referring now to the drawings:

FIG. 1 shows an artists depiction of a preferred form or embodiment of the invention, as it is presently contemplated in an improved apparatus 10, hereinafter referred to as remediation apparatus 10, for the remediation of toxic flue gas pollutants, and is shown aligned for passing exhaust therefrom to a bag house 11. The exhaust, as the invention is suitable for use with, can be a flue gas flow that originates in a plant, such as a coal fired power plant, shown as boiler 13 in FIG. 2, that passes a flue gas through a line 13a, shown in broken lines, and identified as arrow A, that contains pollutants, such as sulphur dioxide ($SO_2$). Said pollutants are removed by the apparatus of and in a practice of the method of the invention shown herein as a best mode. In which practice, pollutant particulates that are compacted with fine sorbent particles in a line section of the apparatus 10, as discussed in detail hereinbelow, that provides for impacting flows that create turbulence and provide for a thorough mixing during passage therethrough, forming an agglomerized mix of particulates are then moisturized for separation out of the flue gas flow in a bag house, centrifuge, fluidized bed, water system, or a like agglomerized particulate removal apparatus, for disposal.

Figure 2:
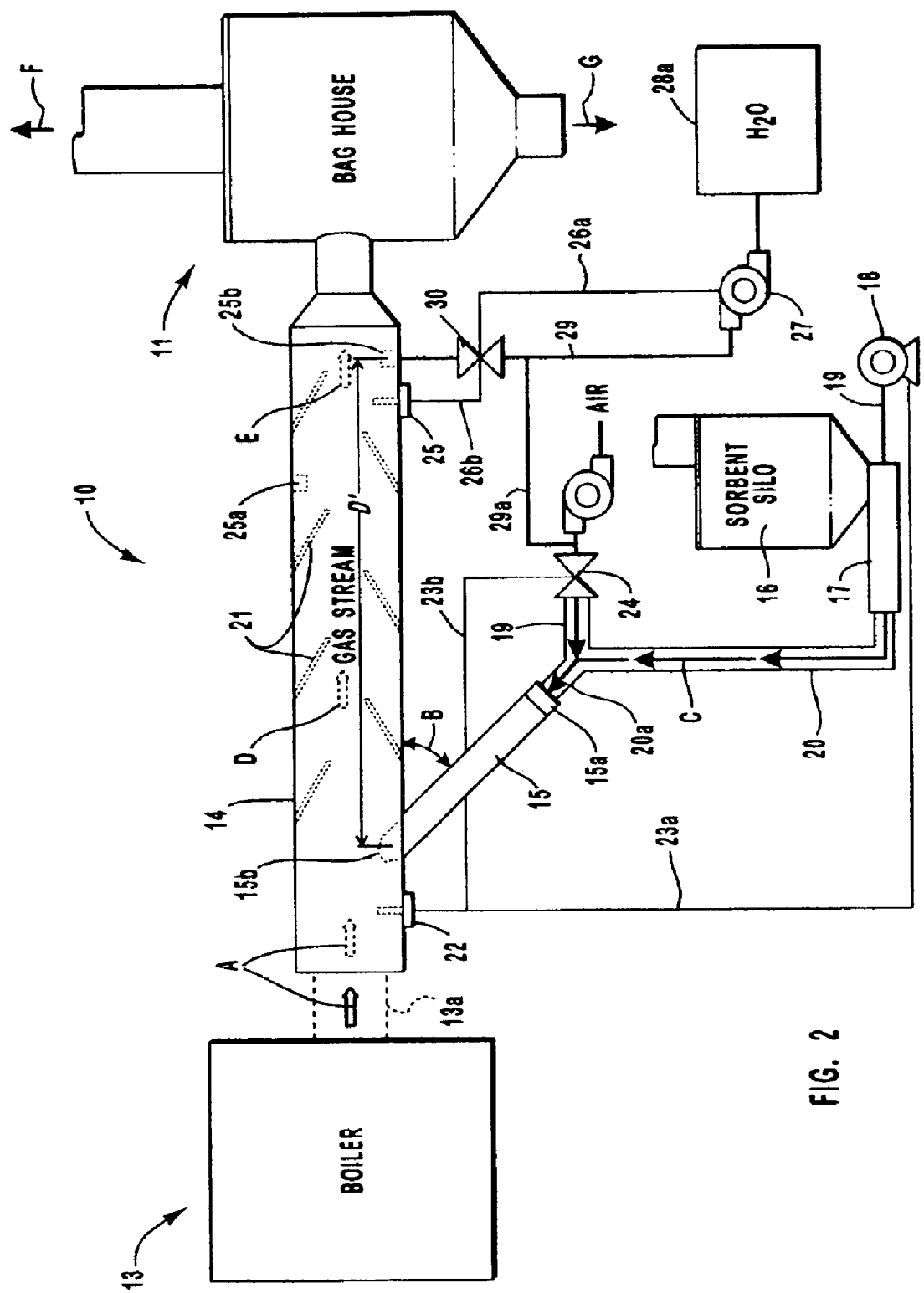
FIG. 2 is a schematic side elevation sectional view of the remediation apparatus of FIG. 1 shown as part of a system for the remediation of toxic flue gas pollutants.

A boiler 13 is shown in the schematic of FIG. 2 passes the flue gas flow, arrow A, through line 13a, illustrated in broken lines. Which flow is a waste gas as is produced from burning fossil fuels as in a coal fired power plant, for example, with the gas flow, arrow A, containing toxic pollutants and enters a manifold 14 of the remediation apparatus 10, shown in FIG. 1. The flow, arrow A, includes sulfur dioxide ($SO_2$) that must be removed before the gas flow is vented to atmosphere. That toxic pollutant emissions, such as those containing sulfur dioxide ($SO_2$), should not be vented directly into the atmosphere is without question and, in practice, with a utilization of the apparatus 10 of the invention, ninety (90)

to ninety-seven (97) and greater percent of pollutant particles have been removed. This is in contrast to earlier state of the art remediation systems that have, in practice, removed up to seventy percent and usually less of sulphur dioxide pollutant ($SO_2$) as have been present in a power plant flue gas, to include electrostatic charging systems, earlier compaction systems, water scrubbers, and the like.

The invention improves upon all earlier remediation systems and does so with a much simplified apparatus than that involved in earlier systems and provides a simple and reliable method for its use. Shown in FIG. 1, is an artists conception drawing of the improved apparatus for the remediation of toxic flue gas pollutants 10 of the invention that is hereinafter referred to as remediation system 10. The remediation system 10 is shown installed, on one end, to line 13a from boiler 13 and on the other, to a pollutant particulate removal facility such as a bag house facility 11, through, it should be understood, within the scope of this disclosure, the compacted and moisturized particulates as are produced in the remediation system 10 of the invention can be handled and refined from the gas flow in a number of particulate removal facilities that are in addition to bag house 11, to included, but not limited to, a centrifuge system, a moving bed assembly, water bath system, or the like, not shown.

The apparatus of the invention provides for a compacting of, respectively, toxic pollutant particles, here shown as sulphur dioxide ($SO_2$), with particles of a sorbent material that will readily combine or agglomerated with such pollutant particles. Specifically, in practice, lime, ground to a fine consistency has been used as the preferred sorbent material for injection into a flue gas flow containing sulphur dioxide ($SO_2$) at a feed rate of approximately 2.1 PPM lime to 1 PPM of $SO_2$. With a use of the remediation apparatus 10 of the invention, this operation results in a removal of from ninety (90) to ninety-seven (97) percent of the sulfur dioxide ($SO_2$), when the agglomorized flow from the remediation apparatus 10 is processed in a bag house that receives the flue gas stream, arrow E in the Figs., as set out below.

The above set out removal rate constitutes a very significant improvement over operations of all other earlier compacting and electrostatic charging systems. In practice, a counter-current injection of the lime particulates as have been fine ground to from fifty (50) to one hundred fifty (150) mesh and to an even smaller mesh of approximately three hundred fifty (50) mesh, depending upon the agglomorized particulate removal system as is employed. In a practice of the invention lime particulates are injected under pressure in a direction that is counter-current to the flue gas flow. This injection, as shown in the schematic of FIG. 2, is through an injector 15, that is shown as a straight tube, and is fitted into a system duct or manifold 14, that is shown as an open cylinder. The injector 15, shown as a tube or pipe, is maintained at an angle B, that is to the manifold 14 longitudinal axis. The selected angle is preferably an angle from thirty (30) to sixty (60) degrees that the injector 15 center longitudinal axis makes to the outer surface of the manifold 14, and point back into the flue gas flow, arrow A in FIG. 2. The injector 15 provides a sorbent material flow that is directed into, to impact and thoroughly mixed with the flow of toxic flue gas pollutants, arrow A in FIG. 1. The manifold 14, as shown, is preferably an open cylinder, though another appropriate shape of tube or cylinder can be so used, within the scope of this disclosure. So arranged, the sorbent material, that is preferably the finely ground lime particulates selected from a family that includes hydrated lime, quick lime, limestone, or the like. However, for some applications that are not specifically discussed herein, the selected sorbent material may be a non-lime material such as a phosphorus mixture, carbon compound, a compound containing ammonia, or the like, within the scope of this disclosure. In practice, the selected sorbent material is injected, under a pressure of from six (6) to ten (10) psi, as a counter-current flow into the flue gas flow, shown as arrow A. The selected sorbent materials are fine ground to, preferably, a size range of from fifty (50) to one hundred fifty (150) mesh. Though, for some applications, a preferred size of sorbent particles may be larger or smaller within the scope of this disclosure. A flow of sorbent materials, as shown in FIGS. 1 and 2, is gravity fed out from a bin or hopper 16 to pass into a feeder 17 that receives pressurized air flow that is passed thereto through a line 19 from a pump 18, as shown in FIG. 2. Shown in FIG. 2, the pressurized air flow with the entrained sorbent material particles is then passed, shown as arrow C, through feed line 20 and into and through the injector 15 feed tube. This flow, arrow C, is pressurized appropriately to take into account the pressure of the flue gas flow so as to create turbulence in opposing flows, so as to tumble and thoroughly mix the sorbent material particles into, to compact and agglomorize with, the flue gas toxic pollutant particles, in particular sulfur dioxide ($SO_2$). Which sorbent material pressurization is selected so as not to over-power that flue gas flow, with the combined flows than continuing, shown as arrow D, through the manifold 14. So arranged, the toxic pollutant and sorbent material particulates vigorously are maintained together, tumbling and agglomorizing together along the manifold 14 between the injector 15 end 15b and a moisture injector 25b, as shown in FIG. 2, and as discussed further herein. Which distance, D', to provide a thorough and complete mixing is from twenty (20) to thirty (30) feet between injector end 15b and the moisture injector. Over this distance D', the sorbent material and flue gas particles are thoroughly mixed, the respective particles engaging one another and are compacted and agglomerized together. Optionally, within the scope of this disclosure and for the makeup of a particular flue gas flow, the manifold 14 can include spaced fins 21, shown in broken lines, that are secured along connecting edges of each to project at an angle outwardly from the manifold 14 interior wall. Which project angle for each fin is an angle that is less than ninety (90) degrees to the flue gas flow. The fins 21 are provided, as needed, to further encourage turbulence and a mixing of the particulates in the flow. While the fins 21, for most applications, are not needed, they are included herein as an optional inclusion.

As set out above, the injection of the sorbent particulates into the flue gas stream is counter-current thereto and at a pressure that is selected so as not to interrupt, or will create a back pressure in, the flue gas flow, arrow A. Accordingly, as needed, a gas flow temperature and pressure first sensor 22 can be provided at the flue gas inlet end of the manifold 14, as shown in FIG. 2, to sense gas flow pressure and temperature, and which first sensor 22 is preferably also configured to read moisture content as is present in the flue gas. Where a consistent flue gas flow pressure is exhibited and where the flue gas water content does not very greatly, the first sensor 22 need not be used, and while a reading of flue gas moisture content may be desirable, for most applications, it is not required. Where, however, such first sensor 22 is employed, it is electrically connected, shown at line 23a, to the blower 18 to provide for controlling pressure and volume of the sorbent materials flow that is injected into the flue gas, illustrated by arrow A. Further, where a flue gas flow is sensed as being dry so as to require an initial moisture addition, a water mist can be injected into the incoming flue gas to produce a desired moisture content to the mix of the sorbent and pollutant particulates, as discussed hereinbelow.

To provide moisture addition to the flue gas flow into the manifold 14, as shown in FIG. 2, the first sensor 22 is electrically connected through a line 23b to a valve 24 to command valve opening to pass a pressured flow of a water mist through line 29a, and into and through valve 24 and through line 19 to mix into the sorbent material flow as is passed through line 20. The moisturized sorbent materials flow to travel through line 20a and into injector 15 for mixing with the sorbent material with the combined air and sorbent material flow to pass out of the injector 15 end 15b, as a counter current flow to the flue gas flow, shown as arrow A.

The flow of agglomerized sorbent and pollutant particulates travel downstream from the sorbent injector 15, arrow D, for a traveling distance D' that is from twenty (20) to thirty (30) feet, and passes across a moisture sensor 25 that extends through the manifold 14 wall and into the flue gas flow. The distance D' is the spacing distance between the injector end 15b and the second sensor 25 that measures the moisture content of the mixed flow and, when that moisture content is below eighteen (18) percent humidity, passes a signal through lines 26a and 26b to command operation of pump 27. Pump 27 provides a pressurized water flow from a reservoir 28a, to operate a valve 30 located in line 29 from the water reservoir 28a that opens to direct the flow of water through a nozzle that produces a fine mist that is injected into the flue gas and sorbent material mix flow, arrow E. Which moisture injection is to elevate the moisture content to from eighteen (18) to twenty (20) percent humidity, with the moisturized flow then traveling to a bag house 11, like that shown in FIG. 3, wherein the agglomerized and moisturized particles are removed from the flow, as set out and discussed below.

In practice, water is injected through a nozzle 25b, shown in broken lines in FIG. 2, as a fine or atomized water mist that is distributed throughout and is thoroughly mixed into the flue gas flow, arrow E. The mist contains droplets that range in size from ten (10) to fifteen (15) microns, and is of a volume to achieve an optimum flue gas mix flow humidity level that is uniform throughout. Which humidified mix of sorbent and pollution particulates in the flue gas flow, arrow E, is then passed into a particulate removal facility, such as the bag house 11, of FIGS. 1 and 3, wherein the agglomerized sorbent material and pollutant particles are removed.

In a practice of the invention, where fine sorbent material particles are fed into the flue gas flow, arrow A, in a direction of travel against or counter-current to that flow, intense turbulence is created at the junction of the opposing flows, creating a thorough mixing and over the period of residency to the flow over the distance, D' an agglomerization and compaction of the sorbent material particles with pollutant particulates is provided to essentially all the particles that then continue as flue gas flow, arrow D. So arranged, particulate mixing is both thorough and efficient, with at most few un-agglomerized particles found in the flue gas flow, arrow D. This allows for injection of an appropriate volume of sorbent material for the pollutant particles as are actually present in the flue gas flow, arrow A, thereby reducing the volume of sorbent material as is used to only the volume actually needed to provide for a thorough and complete remediation.

Figure 3:
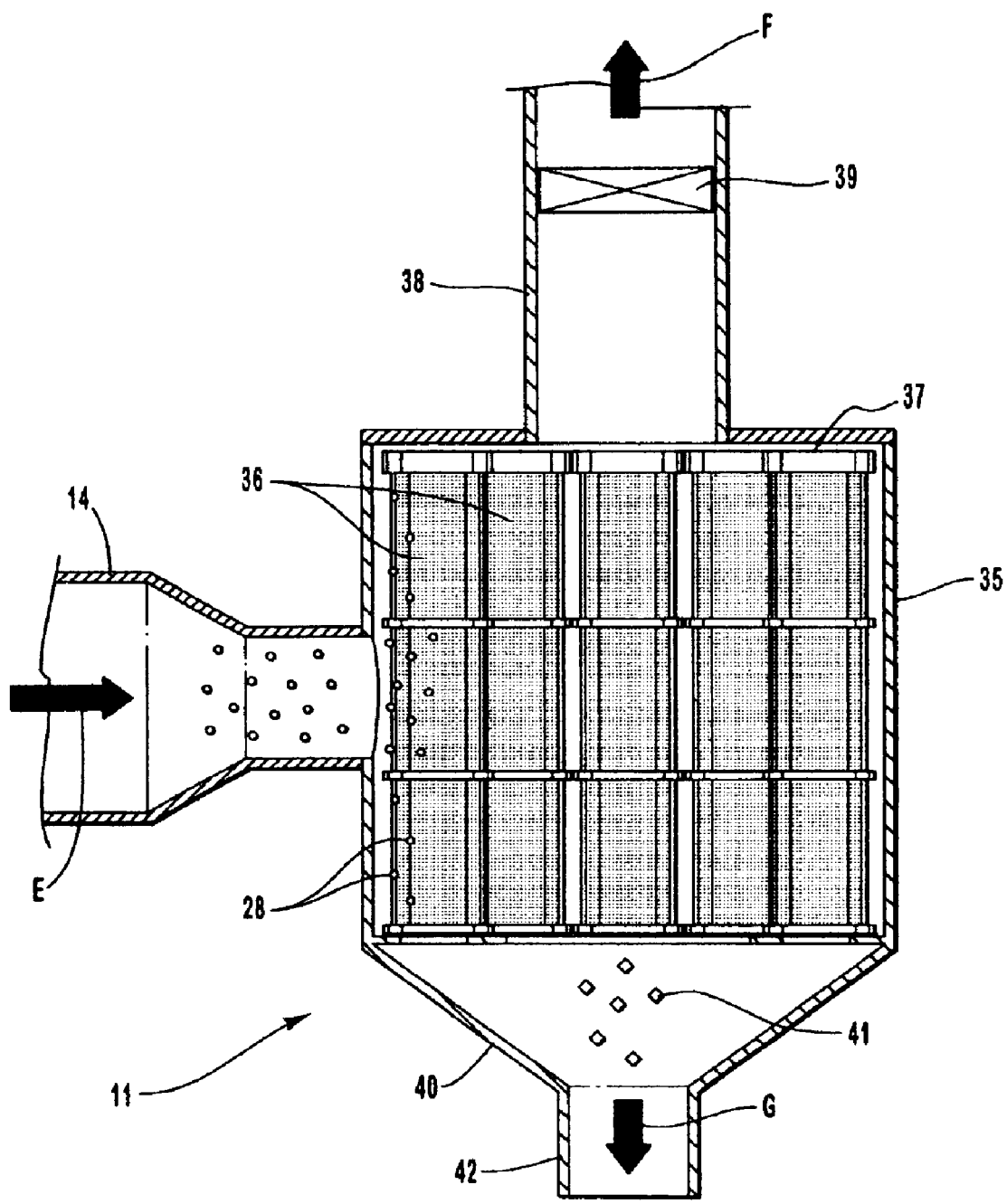
FIG. 3 is a is a front sectional view of the bag house taken along the line 3—3 of FIG. 1.

The bag house 11, as shown best in FIG. 3, is a preferred precipitate particulate removal facility that, it should be understood, in practice, is a standard unit that includes polyester bags, or bags 36 that are formed to receive the flue gas and agglomorized particulates flows therethrough and are capable of being pulsated to shake collected particles off from the outer surface thereof. Such bag house 11 while preferred for use with the invention, is but one of a number of particulate removal systems as the invention can be used with, to include a centrifuge system, moving bed, water system, or the like, not shown. For such other precipitate removal systems, the optimum humidity or water content of the compacted and humidified flow, arrow E, may vary above or below the preferred moisture content of eighteen (18) to twenty (20) percent that is for use with a bag house 11, as set out above. For example, in a centrifuge particulate removal system, the particulate and water mix can be drier or very wet without a reduction in particulate removal efficiency. Such centrifuge particulate removal systems have, in practice, provide for a removal of from seventy (70) to seventy-five (75) percent of the pollutant particulates from a flue gas flow that is exhausted from the centrifuge system, not shown.

When, however, the remediation apparatus 10 of the invention is employed with a standard bag house 11, like that shown in schematic in FIG. 3, the agglomerized particulate removal efficient is greatly increased to where ninety (90) to ninety-seven (97) and greater percent of toxic pollutants, particularly sulfur dioxide ($SO_2$) particles are removed from the flue gas flow. This removal efficiency is primarily do the both the long residency time in the manifold 14, across distance D', shown in FIG. 2, that the sorbent and toxic pollutant particles experience along with the close control of the flue gas flow agglomerized particles moisture content, arrow E, that enters the bag house 11. So arranged, a maximum percentage to nearly all of the toxic pollutants, particularly sulfur dioxide ($SO_2$), are removed when the flow moisture content is maintained between eighteen (18) and twenty (20) percent.

As set out above, and the bag house 11 preferably utilizes polyester bags 36 that are, in fact, the least expensive bags as are used in conventional bag houses and are most effective when used with the remediation apparatus 10 of the invention for agglomorized particulate removal. This is apparently because the preferred polyester bags 36 are somewhat porous and, with the flue gas flow at the preferred moisture content, a particulate coating is formed on the bag exterior by the entering moist particulates, shown at 28. This particulate coating somewhat fills the bag pores or openings while still allowing for a passage of the gas flow, arrow E. So arranged, nearly all the compacted particulates are captured on the bag surface, with the cleaned flue gas then passed out of the bag necks 37, shown also in FIG. 1, and is vented through a bag house housing vent stack 38, arrow F. Such venting is further encouraged by operation of a vent fan 39 that is turned in that vent stack 38 to pull the now cleaned flue gas flow, arrow F, therethrough. In practice, nearly all the compacted particulates, shown at 41, are removed from the flue gas flow. Thereafter, the compacted agglomorized particulates 41 can be removed, falling off the bag 36 outer surface, when the bag is oscillated and under the urging of gravity. Which removed particulates 41 fall to the bottom of the bag house housing 35 and pass out of a housing lower vent 40, shown as a flow arrow G, to fall into a catchment vessel 42. The collected compacted particles 41 can then be disposed of.

In a practice of the method of the invention to remove toxic particulates, specifically sulphur dioxide ($SO_2$) from a flue gas flow as is produced by a coal fired power plant, a finely ground lime is preferably used as the sorbent material and is fed at a rate of 2.1 parts per million (PPM) of lime per 1.0 PPM of toxic pollutant sulphur dioxide (SO$_2$) particulates into the flue gas flow. The finely ground lime, arrow C, is blown through an adapter 15a located in the sorbent inlet line 15, by operation of blower 18. Shown in FIG. 2, the lime flow passes through the nozzle 15b that is located at the end of the sorbent inlet line 15 and enters into the flue gas flow, arrow A, counter-current to that flue gas flow. The nozzle 15b distributes the finely ground lime flow throughout the flue gas flow, arrow A, that continues through manifold 14, shown as arrow D, providing a residency area across distance D' wherein a thorough mixing and efficient compaction or agglomerization of the sorbent and pollutant particulates occurs. Temperature and moisture content of the flue gas flow, arrow A, can optionally, as needed, be checked at a first or initial sensor 22, that is located in the manifold 14, upstream from the nozzle 15b wherethrough ground lime, under pressure, is passed. The first or initial sensor 22, when present, is connected through line 23a to blower 18, for controlling blower operation to control sorbent transfer, with an addition of water or moisture, when needed, is passed through line 23b by operation of valve 24 that is also connected to first or initial sensor 22. Which sorbent flow and moisture additions are made to the flue gas flow to maintain a desired pressure and moisture content, and may not, depending upon the flue gas make-up, be required. In which case, the sensing temperature and moisture content of the flue gas, arrow A, is not required and first or initial sensor 22 should thereby be considered to be optional.

The injected lime, as set out above, is preferably finely ground to between one hundred fifty (150) to three hundred fifty (350) mesh with, when separation of the agglomerized particles from the flue gas flow, arrow E, is to take place in a bag house, it must be finely ground to the smaller end of the range three hundred fifty (350) mesh. Whereas, the lime can be ground to the larger range of from fifty (50) to one hundred fifty (150) mesh when another separation apparatus, such as a centrifuge system, is to be employed. Accordingly, for a practice of the method of the invention in the removal apparatus as the invention can be used with, the sorbent material particulates should be of a size of from fifty (50) to one hundred fifty (150) and up to three hundred fifty (350) mesh.

As set out above, where the pressure and moisture content of the flue gas flow, arrow A, are consistent, a sensing of the moisture content and water addition is required only after the mixing of the sorbent materials into the flue gas flow, and with the flue gas flow containing agglomerized particulates of pollutants and sorbent material, arrow D. To provide which sensing, a moisture sensor 25 is, as shown in FIG. 2, positioned downstream from where the sorbent materials are injected into the flue gas flow and is provided to sense and command passage of water, as in a fine mist or in atomized form, into the flue gas flow, arrow D. Such injection is to provide a moisture content in the combined flow of from eighteen (18) to twenty (20) percent humidity, arrow E. This moisture content, where a bag house is to be utilized to separate the agglomerized pollutant and sorbent particles, is critical. Whereas, where a particle separation is performed in other than a bag house, such as a centrifuge system, the range of moisture content can be broader. In practice, where a particle separation system other than a bag house is utilized, the flue gas flow, arrow E, can have a moisture content of from twenty (20) to twenty-five (25) percent. Which different moisture content, it should be understood, is still within the scope of this disclosure. To promote a thorough and uniform mixing of the injected moisture into the flue gas flow, arrow D, the water is urged, under a pressure of from forty (40) to sixty (60) psi, by compressed air, out through nozzle 25a as a fine mist having a droplet size from ten (10) to fifteen (15) microns.

As set out above, the invention provides a thorough and complete mixing of the injected sorbent materials with toxic pollutant particulates over the distance D'. In addition to the turbulence and mixing provided by the described counter-current injection of the fine sorbent particles into the flue gas flow and the long residency period of turbulence over distance D', further turbulence can be created with an inclusion of fins or baffles 21 in the manifold 14 that are secured at spaced intervals to the inner wall of the manifold, projecting into angled or sloping in the direction os the flue gas flow. The baffles 21, depending upon the efficiency of mixing by the counter-current injection of the sorbent materials into flue gas flow, arrow A, and residency period over distance D', may not be needed. If, however, such are employed, they are preferably mounted to the manifold 14 inner wall at approximately an angle of from thirty (30) to thirty-seven (37) degrees sloping in the direction of flue gas flow.

While a preferred embodiment of the invention in an improved method and apparatus for the remediation of toxic flue gas pollutants has been shown and described herein, it should be understood that the present disclosure is made by way of example only and that variations to the invention as disclosed and method are possible within the scope of this disclosure without departing from the subject matter coming within the scope of the following claims and a reasonable equivalency thereof, which claims I regard as my invention.

I claim:

1. An apparatus for removing particulate matter and pollutants from a gas stream comprising, a duct having a gas inlet first end connected to receive a gas stream containing pollutant particles, said duct defining a straight passageway between said first end and a second end that connects to vent particulates into a particulate removal means, said duct having a length and a sorbent material injector means fitted into a duct side at a sorbent introduction site, with said sorbent material injector means having a nozzle end located within the duct that is to pass particles of a sorbent material into, and counter-current to, a flue gas flow, passing through said duct that contains pollutant particles, providing mixed and compacted sorbent material and pollutant particles; a moisture sensor means installed in said duct downstream from said injector means nozzle end to read moisture content of the gas stream containing said mixed and compacted sorbent material and pollutant particles; moisture injector means fitted into said duct downstream from said moisture sensor means and spaced from twenty to thirty feet from said sorbent material injector means nozzle end for injecting water, as a mist, into said gas stream containing said mixed and compacted sorbent material and pollutant particles, which said moisture injector means is connected to a source of water and is operated in response to a sensing, by said moisture sensor means, of a requirement to moisturize said gas stream containing said mixed and compacted sorbent material and pollutant particles to provide a moisture content thereto that is a percentage of from eighteen to twenty percent of saturation, and which said moisture is injected into said mixed and compacted sorbent material and pollutant particles prior to its passage into a removal means; removal means for removing said mixed and compacted sorbent material and pollutant particles.

2. The apparatus as recited in claim 1, wherein the moisture injector means that is located in the duct, twenty to thirty feet downstream from the sorbent material delivery means, is connected to operate on command from the moisture sensor means, to pass a moisture flow into said duct, to provide moisture to said mixed and compacted sorbent material and pollutant particles, downstream from said sorbent injector means, to raise the moisture content so as to promote reaction of said mixed and compacted sorbent material and pollutant particles that pass into the removal means.

3. An apparatus as recited in claim 2, wherein the moisture injector means includes a nozzle that provides water, as a fine water mist, into said mixed and compacted sorbent material and pollutant particles.

4. An apparatus as recited in claim 3, wherein moisture is passed through a nozzle end of the moisture injector means as a fine water mist into the mixed and compacted sorbent material and pollutant particles to provide a moisture content of from eighteen to twenty percent of a saturation humidity.

5. An apparatus as recited in claim 4, wherein the moisture injector means includes a nozzle end arranged to inject a mist of water droplets that have diameters of from ten to fifteen microns.

6. An apparatus as recited in claim 1, wherein said removal means is a bag house system connected by a vent to the second end of the duct passageway, and said bag house includes a plurality of bags having open ends therethrough the mixed and compacted sorbent material and pollutant particles are directed, and each bag is formed from a bag material having pores that each function as a site for receiving the mixed and compacted sorbent material and pollutant particles.

7. An apparatus as recited in claim 1, wherein sorbent material is selected for its reaction capability with particulate matter of the flue gas stream and is ground to a fine consistency of from one hundred fifty to three hundred fifty mesh.

8. An apparatus as recited in claim 1, wherein said sorbent material is a hydrated lime, quick lime or limestone.

9. An apparatus as recited in claim 1, further including an initial sensor means for measuring gas flow pressure and temperature that is located in the duct upstream from the sorbent material injector means to measure the entering flue gas stream temperature, pressure and moisture content as are present in said flue gas stream prior to introduction of sorbent material therein.

10. An apparatus as recited in claim 9, wherein the initial sensor means is connected to control operation of the sorbent material injector means to increase or decrease sorbent material volume of flow and pressure, and to control operation of a valve that is opened on command of said initial sensor means to pass a moisture flow into said sorbent material passing into said sorbent material injector means.

11. An apparatus as recited in claim 1, further including at least one static fin or plate, secured along a coupling edge thereof to a duct inner wall, extending from said duct inner wall toward said duct longitudinal center axis, and slanting with the direction of flue gas stream flow at an angle from said duct inner wall that is less than ninety degrees.

12. An apparatus as recited in claim 1, wherein the sorbent material injector means includes a straight tube that is fitted through and secured at its outer surface to the duct so as to form an angle of from thirty to sixty degrees to the duct interior wall, sloping into the gas stream flow.

* * * * *